US012569346B2

(12) United States Patent
Courtade-Jouanicq et al.

(10) Patent No.: US 12,569,346 B2
(45) Date of Patent: *Mar. 10, 2026

(54) PATIENT-SPECIFIC BONE FRACTURE PROSTHESES AND METHODS OF MAKING THE SAME

(71) Applicant: HOWMEDICA OSTEONICS CORP., Mahwah, NJ (US)

(72) Inventors: Celine Courtade-Jouanicq, Montpelier (FR); Marine Godelu, Grenoble (FR); Vincent Coulange, Lyons (FR); Shawn M. Gargac, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,609

(22) Filed: Apr. 24, 2024

(65) Prior Publication Data

US 2024/0277481 A1 Aug. 22, 2024

Related U.S. Application Data

(62) Division of application No. 16/967,374, filed as application No. PCT/US2019/016702 on Feb. 5, 2019, now Pat. No. 12,090,057.

(Continued)

(30) Foreign Application Priority Data

Feb. 6, 2018 (EP) ..................................... 18305118

(51) Int. Cl.
| | |
|---|---|
| *A61F 2/30* | (2006.01) |
| *A61B 17/72* | (2006.01) |
| *A61F 2/40* | (2006.01) |

(52) U.S. Cl.
CPC .......... *A61F 2/30942* (2013.01); *A61B 17/72* (2013.01); *A61F 2/4014* (2013.01);
(Continued)

(58) Field of Classification Search
CPC ........... A61F 2/40–2002/4096; A61F 2/30942; A61F 2002/30985; A61F 2/30988; A61B 34/10; A61B 2034/108
See application file for complete search history.

(56) References Cited

U.S. PATENT DOCUMENTS

| | | |
|---|---|---|
| 4,305,394 A | 12/1981 | Bertuch, Jr. |
| 4,433,686 A | 2/1984 | Charnley |

(Continued)

FOREIGN PATENT DOCUMENTS

| | | | | |
|---|---|---|---|---|
| AU | 2004316388 B2 * | 1/2011 | .......... | A61F 2/4059 |
| CA | 2209498 A1 | 8/1996 | | |

(Continued)

OTHER PUBLICATIONS

First Office Action issued in connection with Chinese Patent Application No. 201910110195.8, Feb. 21, 2024, 12 pages.
(Continued)

*Primary Examiner* — Alvin J Stewart
(74) *Attorney, Agent, or Firm* — DUANE MORRIS LLP

(57) ABSTRACT

Provided is a method for manufacturing a prosthesis for a fractured long bone of a patient. The method includes: providing data representative of the fractured long bone of the patient, the fractured long bone comprising a diaphyseal fragment comprising a medullary cavity; based on the data provided, designing the prosthesis specifically to the patient, wherein the prosthesis comprising a stem part configured to be inserted into the medullary cavity for securing the stem part to the diaphyseal fragment.

13 Claims, 5 Drawing Sheets

Related U.S. Application Data

(60) Provisional application No. 62/669,850, filed on May 10, 2018.

(52) U.S. Cl.
CPC .. *A61F 2/4059* (2013.01); *A61F 2002/30556* (2013.01); *A61F 2002/30579* (2013.01); *A61F 2002/30617* (2013.01); *A61F 2002/30878* (2013.01); *A61F 2002/30948* (2013.01); *A61F 2002/30952* (2013.01); *A61F 2002/4007* (2013.01); *A61F 2002/4018* (2013.01); *A61F 2002/4022* (2013.01); *A61F 2002/4029* (2013.01); *A61F 2002/4051* (2013.01); *A61F 2002/4062* (2013.01); *A61F 2002/4066* (2013.01); *A61F 2002/4077* (2013.01); *A61F 2310/00359* (2013.01)

(56) References Cited

U.S. PATENT DOCUMENTS

| | | | |
|---|---|---|---|
| RE31,865 E | 4/1985 | Roux | |
| 4,662,891 A | 5/1987 | Noiles | |
| 4,904,265 A | 2/1990 | MacCollum et al. | |
| 5,030,219 A | 7/1991 | Matsen, III et al. | |
| 5,284,483 A | 2/1994 | Johnson et al. | |
| 5,534,032 A | 7/1996 | Hodorek | |
| 5,609,642 A | 3/1997 | Johnson et al. | |
| 5,630,819 A | 5/1997 | Ashby et al. | |
| 5,634,927 A | 6/1997 | Houston et al. | |
| 5,702,477 A | 12/1997 | Capello et al. | |
| 5,779,710 A | 7/1998 | Matsen, III | |
| 5,976,147 A | 11/1999 | LaSalle et al. | |
| 6,117,138 A | 9/2000 | Burrows et al. | |
| 6,143,012 A | 11/2000 | Gausepohl | |
| 6,152,930 A | 11/2000 | Mastrorio | |
| 6,267,785 B1 | 7/2001 | Masini | |
| 6,283,999 B1 * | 9/2001 | Rockwood, Jr. | A61F 2/40 623/19.12 |
| 6,334,874 B1 * | 1/2002 | Tornier | A61F 2/4014 623/19.14 |
| 6,398,812 B1 * | 6/2002 | Masini | A61F 2/4059 623/19.14 |
| 7,353,153 B2 | 4/2008 | Ascenzi et al. | |
| 7,435,263 B2 * | 10/2008 | Barnett | A61F 2/3804 623/19.12 |
| 7,527,631 B2 | 5/2009 | Maroney et al. | |
| 7,699,853 B2 * | 4/2010 | Durand-Allen | A61B 17/8883 623/22.12 |
| 8,062,299 B2 | 11/2011 | McGahan et al. | |
| 8,078,440 B2 | 12/2011 | Otto et al. | |
| 8,277,450 B2 | 10/2012 | Dees, Jr. et al. | |
| 8,545,506 B2 | 10/2013 | Long et al. | |
| 8,562,616 B2 | 10/2013 | May et al. | |
| 8,574,235 B2 * | 11/2013 | Stone | A61B 17/842 623/22.11 |
| 8,768,674 B2 | 7/2014 | Darwish et al. | |
| 9,271,744 B2 | 3/2016 | Meridew | |
| 9,408,616 B2 | 8/2016 | Kehres et al. | |
| 9,498,233 B2 | 11/2016 | Eash | |
| 9,662,219 B2 | 5/2017 | Bonin, Jr. et al. | |
| 9,763,682 B2 | 9/2017 | Bettenga | |
| 10,987,175 B2 * | 4/2021 | Britton | A61B 34/70 |
| 11,229,524 B2 * | 1/2022 | Sperling | A61F 2/4059 |
| 11,266,503 B2 * | 3/2022 | Coulange | A61F 2/4014 |
| 11,559,405 B2 * | 1/2023 | Yadav | A61F 2/4003 |
| 11,703,096 B2 | 7/2023 | Denhard et al. | |
| 12,090,057 B2 * | 9/2024 | Courtade-Jouanicq | A61B 17/72 |
| 2003/0014119 A1 | 1/2003 | Capon et al. | |
| 2003/0060889 A1 | 3/2003 | Tarabishy | |
| 2003/0078669 A1 | 4/2003 | Martin et al. | |
| 2004/0162619 A1 | 8/2004 | Blaylock et al. | |
| 2005/0101961 A1 | 5/2005 | Huebner et al. | |

| | | | |
|---|---|---|---|
| 2005/0107797 A1 | 5/2005 | Romeo | |
| 2005/0177241 A1 * | 8/2005 | Angibaud | A61F 2/4059 623/19.14 |
| 2006/0009854 A1 | 1/2006 | Justin et al. | |
| 2006/0015188 A1 | 1/2006 | Grimes | |
| 2007/0244565 A1 | 10/2007 | Stchur | |
| 2008/0004517 A1 | 1/2008 | Bhandarkar et al. | |
| 2008/0015599 A1 | 1/2008 | D'Alessio | |
| 2009/0265010 A1 * | 10/2009 | Angibaud | A61F 2/4059 623/19.11 |
| 2009/0318927 A1 | 12/2009 | Martin et al. | |
| 2010/0217400 A1 * | 8/2010 | Nortman | A61B 34/25 623/20.14 |
| 2010/0234850 A1 | 9/2010 | Dees, Jr. et al. | |
| 2011/0224673 A1 | 9/2011 | Smith | |
| 2011/0224799 A1 | 9/2011 | Stone | |
| 2011/0282462 A1 | 11/2011 | Wunderle et al. | |
| 2012/0035733 A1 * | 2/2012 | Porter | A61F 2/3804 623/18.11 |
| 2013/0006253 A1 | 1/2013 | Waite, II et al. | |
| 2013/0041376 A1 | 2/2013 | Neal et al. | |
| 2013/0204259 A1 | 8/2013 | Zajac | |
| 2013/0261622 A1 | 10/2013 | Bonjour et al. | |
| 2013/0325136 A1 | 12/2013 | Thomas et al. | |
| 2013/0325430 A1 | 12/2013 | Darwish et al. | |
| 2014/0074174 A1 | 3/2014 | Schacherer et al. | |
| 2014/0276850 A1 | 9/2014 | Chaney et al. | |
| 2014/0276857 A1 | 9/2014 | Major | |
| 2014/0330390 A1 | 11/2014 | Liu et al. | |
| 2014/0363481 A1 | 12/2014 | Pasini et al. | |
| 2015/0190151 A1 | 7/2015 | Budhabhatti et al. | |
| 2015/0190237 A1 | 7/2015 | Bonin, Jr. et al. | |
| 2015/0250601 A1 | 9/2015 | Humphrey | |
| 2015/0313727 A1 | 11/2015 | Waite, II et al. | |
| 2016/0158021 A1 | 6/2016 | Goldberg et al. | |
| 2016/0287395 A1 | 10/2016 | Khalili et al. | |
| 2017/0000503 A1 | 1/2017 | Keefer et al. | |
| 2017/0007275 A1 | 1/2017 | Park et al. | |
| 2017/0079800 A1 | 3/2017 | Messieh | |
| 2017/0239058 A1 | 8/2017 | Goldberg | |
| 2017/0333215 A1 | 11/2017 | Wolfson et al. | |
| 2018/0250138 A1 | 9/2018 | Alidousti et al. | |
| 2018/0318093 A1 | 11/2018 | Kirwan | |
| 2019/0015119 A1 | 1/2019 | Athwal et al. | |
| 2019/0105169 A1 * | 4/2019 | Sperling | G16H 30/20 |
| 2019/0167356 A1 * | 6/2019 | Britton | A61B 90/50 |
| 2019/0231544 A1 | 8/2019 | Boileau et al. | |
| 2019/0240030 A1 * | 8/2019 | Coulange | A61B 17/72 |
| 2019/0298543 A1 | 10/2019 | Hashida et al. | |
| 2021/0244546 A1 * | 8/2021 | Yadav | A61F 2/30942 |
| 2022/0142784 A1 * | 5/2022 | Coulange | A61F 2/30942 |
| 2023/0090775 A1 * | 3/2023 | Yadav | A61F 2/4003 623/19.14 |
| 2023/0101690 A1 | 3/2023 | Harder et al. | |
| 2024/0277481 A1 * | 8/2024 | Courtade-Jouanicq | A61F 2/4014 |
| 2024/0341966 A1 * | 10/2024 | Yadav | A61F 2/4059 |

FOREIGN PATENT DOCUMENTS

| | | | |
|---|---|---|---|
| CN | 105263446 A | 1/2016 | |
| DE | 19532898 A1 | 3/1997 | |
| EP | 1269941 A1 | 1/2003 | |
| EP | 1048274 B1 | 9/2012 | |
| EP | 2769700 A1 * | 8/2014 | A61F 2/40 |
| EP | 2668928 B1 | 3/2015 | |
| EP | 2623045 B1 | 9/2015 | |
| FR | 2939639 A1 * | 6/2010 | A61F 2/4014 |
| FR | 2939639 B1 * | 6/2010 | A61F 2/40 |
| FR | 2965712 A1 * | 4/2012 | A61F 2/4014 |
| JP | 2013521889 A | 6/2013 | |
| TW | I606813 B | 12/2017 | |
| WO | 2008036831 A2 | 3/2008 | |
| WO | 2014035991 A1 | 3/2014 | |
| WO | 2016094739 A1 | 6/2016 | |
| WO | WO-2018175897 A1 * | 9/2018 | B22F 10/20 |

(56) References Cited

FOREIGN PATENT DOCUMENTS

| | | | |
|---|---|---|---|
| WO | 2019156985 | A1 | 8/2019 |
| WO | 2020072466 | A1 | 4/2020 |

OTHER PUBLICATIONS

First Office Action issued in connection with Canadian Patent Application No. 3,089,708, Jun. 7, 2024, 9 pages.

Non-Final Office Action issued in connection with U.S. Appl. No. 17/648,963, Feb. 6, 2025, 22 pages.

Extended European Search Report issued in connection with European Patent Application No. 21775719.4, Feb. 20, 2024, 15 pages.

Partial European Search Report issued in connection with European Patent Application No. 21775719.4, Dec. 7, 2023, 13 pages.

Restriction Requirement issued in connection with U.S. Appl. No. 17/276,925, Dec. 13, 2023, 9 pages.

First Office Action issued in connection with Japanese Patent Application No. 2021-518141, Jun. 21, 2022, 3 pages.

International Search Report and Written Opinion dated Mar. 22, 2021 in connection with International Patent Appln. No. PCT/US2021/02343.

International Search Report and Written Opinion of International Patent Application No. PCT/US2019/016702, dated May 6, 2019, in 17 pages.

Final Rejection issued in connection with U.S. Appl. No. 17/276,925, Aug. 5, 2024, 22 pages.

Non-Final Office Action issued in connection with U.S. Appl. No. 17/793,447, Mar. 6, 2023, 13 pages.

Final Office Action issued in U.S. Appl. No. 17/793,447, Jul. 30, 2025, 16 pages.

* cited by examiner

PATIENT-SPECIFIC BONE FRACTURE PROSTHESES AND METHODS OF MAKING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The invention relates to methods for manufacturing patient-specific prostheses for a fractured long bone of a patient and to patient-specific prostheses for a fractured long bone of a particular patient.

Description of the Related Art

US 2004/0230311 A1 discloses a shoulder prosthesis comprising a stem to be inserted into the canal of the diaphyseal fragment of the humerus of a patient, an intermediary part reduced to a medial pillar and a head which is a generally spherical hollow cap. This type of shoulder prosthesis allows reattaching tuberosity fragments and humeral head fragments of the original humerus to the prosthesis.

SUMMARY OF THE INVENTION

For reducing the risk of osteonecrosis of the reattached bone fragments and diaphyseal fragment, it is preferable that these fragments are mechanically loaded in the patient's body. The known shoulder prosthesis do not always ensure that every fragment is appropriately mechanically loaded, since the shape and the size of the fragments differ from one patient to another and do not always correspond to the bone fragments.

The inventions aim to solve the deficiencies of the above-mentioned prior art.

An aim of one or more of the inventions is to provide a new method for manufacturing a prosthesis for a fractured long bone of a patient, reducing the likelihood of osteonecrosis of the reattached bone fragments after implantation into the patient's body.

In another embodiment, data representative of a fractured long bone of a patient is obtained (step A). The data is used for designing (step B) and manufacturing (step C) a patient-specific prosthesis. The prosthesis includes a stem part with patient-specific features that allow, specifically to the patient, distributing mechanical loads onto one or more bone fragments, when the prosthesis is inserted into the patient's body. In other words, the prosthesis is manufactured with a shape tailored to the bone fragment(s). Thus, a patient-specific mechanical stress is applied to the bone fragment(s) when the prosthesis is introduced into the patient's body and during healing of the fracture. The mechanical stress applied to the bone fragment corresponds to conditions that may be planned in advance, prior to the step C of manufacturing the prosthesis. In particular, before the step of manufacturing, the surgeon may choose or plan, specifically to a particular patient, how the bone fragment will be submitted to mechanical stress when the prosthesis is implemented in the patient's body, and the prosthesis is manufactured in a way that this mechanical stress is actually achieved. The risk of post-surgery osteonecrosis is highly reduced, since the bone fragment is mechanically loaded exactly according to the needs of the patient's body.

The stem part may have a shape to be nested into the medullary cavity of the diaphyseal fragment of the patient to whom the prosthesis is intended, although the shape, the bone density and/or other parameters of the diaphyseal fragment may differ from one patient to another. Thanks to its patient-specific nesting shape, the stem part applies an appropriate mechanical stress onto one or more contact zones of the medullary cavity. The mechanical stress to be applied can be chosen in advance, for example by the surgeon, as the patient's data is provided at step A, prior to designing the prosthesis (step B). Thus, the risk of osteonecrosis is reduced after the prosthesis is implemented into the patient.

An aim of the embodiments described herein is to provide new methods for manufacturing a prosthesis for a fractured long bone of a patient, implying fewer chances of osteonecrosis of the reattached bone fragments after implantation into the patient's body.

A method for manufacturing a prosthesis for a fractured long bone of a patient, the method comprising the steps of:
A) providing data representative of the fractured long bone of the patient, the fractured long bone comprising epiphyseal fragments, each epiphyseal fragment preferably being:
  either a tuberosity fragment, secured to a muscle of the patient, the muscle being attached to the tuberosity fragment by means of a tendon of the muscle, or
  an articular fragment, being part of a joint of the patient, for articulating the long bone with an auxiliary bone of the patient;
B) based on the data provided at step A), designing the prosthesis specifically to the patient, the prosthesis comprising a stem part configured for securing the epiphyseal fragments to the stem part, step B) comprising:
  a sub-step of choosing, specifically to the patient, respective securing positions of the epiphyseal fragments relative to each other, representative of how the epiphyseal fragments are planned to be positioned relative to each other when secured to the stem part, the securing positions being chosen so that a respective chosen mechanical stress is applied onto each epiphyseal fragment by at least one of the other epiphyseal fragments, when the epiphyseal fragments are secured at the respective chosen securing positions of the stem part, and
  a sub-step of designing the stem part so that the stem part is configured for securing the epiphyseal fragments at the respective chosen securing positions; and
C) manufacturing the prosthesis including the stem part designed at step B).

In the invention, the data representative of the fractured long bone of the patient (step A) is used for designing (step B) and manufacturing (step C) a patient-specific prosthesis including a stem part with patient-specific features that allow, specifically to the patient, distributing mechanical loads onto the bone fragments, when the prosthesis is inserted into the patient's body. In other words, the prosthesis is manufactured with the most appropriate shape, tailored to the bone fragments. Thus, a patient-specific mechanical stress is applied to the bone fragments when the prosthesis is introduced into the patient's body and during healing of the fracture. The mechanical stress effectively applied to the bone fragments corresponds to conditions that may be planned in advance, prior to the step C of manufacturing the prosthesis. In particular, before the step of manufacturing, the surgeon may choose or plan, specifically to a particular patient, how the bone fragments will be submitted to mechanical stress when the prosthesis is implemented in the patient's body, and the prosthesis is manufactured in a way that this mechanical stress is actually achieved. The risk of post-surgery osteonecrosis is highly reduced, since the bone fragments are mechanically loaded according to the needs of the specific patient.

The stem part is built so that the epiphyseal fragments may be reattached at predetermined respective securing positions by the surgeon. Preferably, the stem part is configured with a patient-specific shape and features, such that the epiphyseal fragments can only be reattached at these respective securing positions. When positioned in this way, a patient-specific mechanical stress is applied by the bone fragments to each other. In this method, the stress applied on the bone fragments is chosen prior to designing the prosthesis, due to the data representative of the patient. This method ensures that the manufactured prosthesis, intended for a respective patient, will apply the intended mechanical stress to the fragments, even if the fragments differ from one patient to the other, in terms of shape, bone density or other parameters. This provides a reduction in the risk of osteonecrosis when the prosthesis is implemented in the specific patient.

Further optional and advantageous features of the invention are defined below:

Step B) comprises the further sub-step of designing the stem part so that the stem part comprises a visible mark indicating the respective securing positions of the epiphyseal fragments on the stem part.

Step B) comprises the further sub-step of designing the stem part based on the data provided at step A), so that the stem part comprises, specifically to the patient, coverable epiphyseal portions, being configured for being covered respectively by the epiphyseal fragments when the epiphyseal fragments are secured to the stem part at the respective chosen positions; wherein the visible mark is designed so as to visually delimit the coverable epiphyseal portions from each other.

The stem part comprises, for at least one of the epiphyseal fragments, a respective plug, for securing the concerned epiphyseal fragment to the stem part, said at least one plug applying mechanical stress onto the epiphyseal fragment secured thereto.

Another object of the invention is defined as follows:

A patient-specific prosthesis for a fractured long bone of a particular patient, the fractured long bone comprising epiphyseal fragments, the prosthesis comprising a stem part that is designed based on data representative of the fractured long bone of this particular patient, the stem part being configured so that each epiphyseal fragment may be secured to the stem part at a chosen securing position relative to the other epiphyseal fragments, the securing positions being chosen based on said data so that, when the epiphyseal fragments are secured at the respective securing positions, a respective chosen mechanical stress is applied onto each epiphyseal fragment by at least one of the other epiphyseal fragments.

Further optional and advantageous features of the invention are defined below:

The stem part comprises, specifically to the patient:
a visible mark indicating the respective securing positions of the epiphyseal fragments on the stem part; and
coverable epiphyseal portions, being configured for being covered respectively by the epiphyseal fragments when the epiphyseal fragments are secured to the stem part at the respective securing positions; wherein the visible mark is designed so as to visually delimit the coverable epiphyseal portions from each other.

The stem part comprises, for at least one of the epiphyseal fragments, a respective plug, for securing the concerned epiphyseal fragment to the stem part, said at least one plug applying mechanical stress onto the epiphyseal fragment secured thereto.

An aim of the invention is to provide a new method for manufacturing a prosthesis for a fractured long bone of a patient, implying fewer chances of osteonecrosis of the reattached bone fragments after implantation into the patient's body.

The invention is defined as follows:

A method for manufacturing a prosthesis for a fractured long bone of a patient, the method comprising the steps of:
A) providing data representative of the fractured long bone of the patient, the fractured long bone comprising:
at least one viable tuberosity fragment, secured to a muscle of the patient, the muscle being attached to said at least one viable tuberosity fragment by means of a tendon of the muscle and
a damaged articular fragment, initially being part of a damaged joint of the patient, for articulating the long bone with an auxiliary bone of the patient;
B) based on the data provided at step A), designing the prosthesis specifically to the patient, the prosthesis comprising:
a stem part, configured for securing said at least one viable tuberosity fragment to the stem part, and
a head part, being configured to be secured to the stem part in replacement for the damaged articular fragment,
step B) comprising:
a sub-step of choosing, specifically to the patient, respective securing positions of said at least one viable tuberosity fragment and of the head part relative to each other, representative of how said at least one viable tuberosity fragment and head part are planned to be positioned relative to each other when secured to the stem part, the securing positions being chosen so that a respective chosen mechanical stress is applied to each of said at least one viable tuberosity fragment by the head part, when said at least one viable tuberosity fragment and the head part are secured at the respective chosen securing positions of the stem part, and
a sub-step of designing the stem part so that said at least one viable tuberosity fragment and the head part may be secured to the stem part at the respective chosen securing positions; and
C) manufacturing the prosthesis including the stem part designed at step B) and providing or manufacturing the head part of the prosthesis.

In the embodiments, the data representative of the fractured long bone of the patient (step A) is used for designing (step B) and manufacturing (step C) a patient-specific prosthesis including a stem part and a head part with patient-specific features that allow, specifically to the patient, distributing mechanical loads onto the bone fragments, when the prosthesis is inserted into the patient's body. In other words, the prosthesis is manufactured with the most appropriate shape, tailored to the bone fragments. Thus, a patient-specific mechanical stress is applied to the bone fragments when the prosthesis is introduced into the patient's body and during healing of the fracture. The mechanical stress effectively applied to the bone fragments corresponds to conditions that may be planned in advance, prior to the step C of manufacturing the prosthesis. In particular, before the step of manufacturing, the surgeon may choose or plan, specifically to a particular patient, how the bone fragments will be submitted to mechanical stress when the prosthesis is implemented in the patient's body, and the prosthesis is manufactured in a way that this mechanical stress is actually achieved in the specific patient. The risk of post-surgery osteonecrosis is highly reduced, since the bone fragments are mechanically loaded according to the needs of the specific patient.

In the embodiments, a head part of standard design, or at least partially of patient-specific design, is used for replacing a damaged fragment and for applying a chosen mechanical stress onto a viable tuberosity fragments. Also, the stem part, including securing positions, is designed so that the viable fragments and the head part may be positioned, or must be positioned, so that the chosen mechanical stress is actually applied when the prosthesis is implanted within the patient. The head part and the stem part, including the securing positions, are designed specifically to one particular patient, based on the data provided at step A), so that mechanical stress tailored to the patient is applied when the prosthesis manufactured at step C) is actually positioned within the patient. This method ensures that every manufactured prosthesis, intended for a respective patient, will apply the intended mechanical stress to the fragments, even if the fragments differ from one patient to the other, in terms of shape, bone density or other parameters. This allows reducing the risk of osteonecrosis when the prosthesis is implemented in the patient.

Further optional and advantageous features of the invention are defined below:

The head part comprises:
a standard cap, comprising an articular surface of concave or convex shape for forming a prosthetic joint for replacement of the damaged joint of the patient, and comprising a securing surface opposed to the articular surface, the standard cap being secured to the stem part by means of the securing surface; and
a patient-specific insert, designed during step B) patient specifically, and manufactured during step C), configured to:
be interposed between the standard cap and the stem part, and
apply the respective mechanical stress onto each of said at least one viable tuberosity fragment.

Another object of the invention is defined as follows:

A patient-specific prosthesis for a fractured long bone of a particular patient, the fractured long bone comprising:
at least one viable tuberosity fragment, secured to a muscle of the patient by means of a tendon of the muscle,
a damaged articular fragment, initially being part of a damaged joint of the patient, for articulating the long bone with an auxiliary bone of the patient;

wherein the prosthesis comprises:
a stem part, configured for securing said at least one viable tuberosity fragment to the stem part, and
a head part, being configured to be secured to the stem part in replacement for the damaged articular fragment,
wherein the stem part is designed based on data representative of the fractured long bone of this particular patient, the stem part comprising securing positions, chosen specifically to this patient based on said data, so that the viable tuberosity fragment and the head part may each be secured to the stem part at a respective securing position, the securing positions being chosen so that, when said at least one viable tuberosity fragment and the head part are secured at the securing positions, a respective chosen mechanical stress is applied onto each viable tuberosity fragment by the head part.

Further optional and advantageous features of the invention are defined below:

The head part comprises:
a standard cap, comprising an articular surface of concave or convex shape for forming a prosthetic joint for replacement of the damaged joint of the patient, and comprising a securing surface opposed to the articular surface, the standard cap being secured to the stem part by means of the securing surface;
a patient-specific insert, designed patient specifically and configured to:
be interposed between the standard cap and the stem part, and
apply the respective mechanical stress onto each of said at least one viable tuberosity fragment.

Further advantages and advantageous features of the invention are disclosed in the following description, provided in reference to the appended drawings, solely for exemplary non-limitative purpose.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

DETAILED DESCRIPTION OF THE PREFERRED EMBODIMENT

Figure 1:
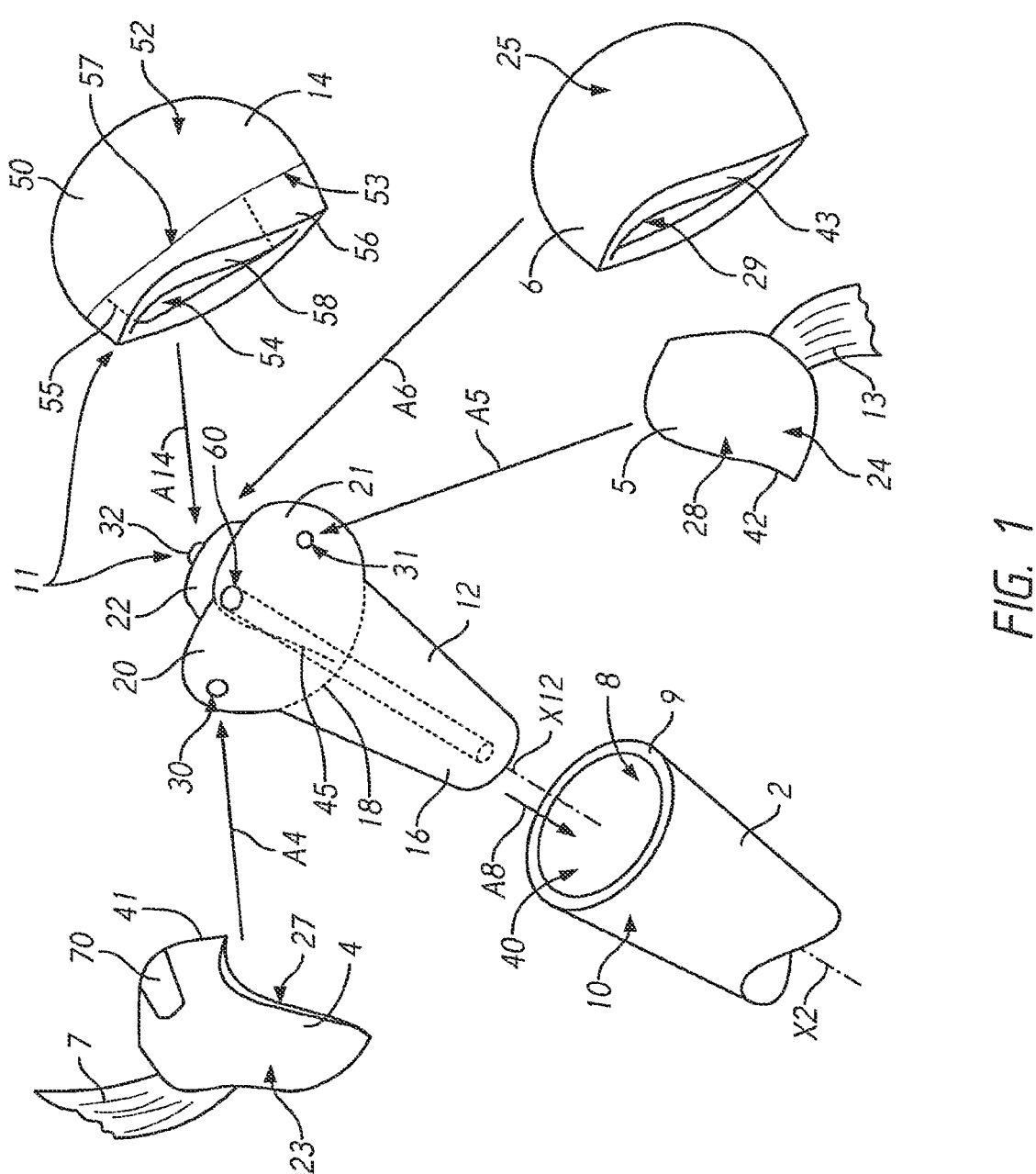
FIG. 1 is an exploded view illustrating aspects of several embodiments.

FIG. 1 shows a fractured long bone of a patient. In the illustration, the fractured long bone is a humerus, broken in four fragments at a proximal (shoulder) end. However, the invention also applies to other long bones of the body, such as the hip end of a femoral bone.

The embodiments preferably are applied to a fractured long bone of a human patient. However, it may be applied to a fractured long bone of an animal patient.

The depicted fractured long bone comprises a diaphyseal fragment 2, or shaft fragment. The diaphyseal fragment 2 includes essentially the shaft part of the original bone.

The fragment 2 defines a diaphyseal axis X2, which is extending along the fragment 2. This fragment 2 is of generally tubular shape around axis X2. The fragment 2 comprises a medullary cavity 8, extending along axis X2, in particular coaxially. The cavity 8 is opened at a proximal end 10 of the fragment 2, where the bone is fractured. In the present case of a humeral diaphyseal fragment 2, the proximal end 10 is defined along axis X2 towards the shoulder joint of the patient, opposite to a distal end of the fragment 2 directed towards the elbow joint of the patient (not shown).

At the proximal end 10, the fragment 2 forms a fracture line 9, delineating the open cavity 8. The fracture line 9 surrounds the axis X2.

The depicted fractured long bone further comprises three epiphyseal fragments 4, 5 and 6. At least one of these fragments 4, 5 and 6 are to be reattached at the end 10 of the fragment 2 for reconstructing the original bone in some embodiments.

Each fragment 4, 5 and 6 respectively has an internal surface 27, 28 and 29, as well as an external surface 23, 24 and 25. The surface 27 of the fragment 4 is opposed to the surface 23. The surface 27 is delimited from the surface 23 by a fracture line 41 of the fragment 4, surrounding surface 23 and surface 27. The surface 28 of the fragment 5 is opposed to the surface 24. The surface 28 is delimited from the surface 24 by a fracture line 42 of the fragment 5, surrounding surface 23 and surface 27. The surface 29 of the fragment 6 is opposed to the surface 25. The surface 29 is delimited from the surface 25 by a fracture line 43 of the fragment 6, surrounding surface 25 and surface 29.

Depending on the fracture type and on the long bone considered, more or less than three epiphyseal fragments may be formed at the end of the patient's long bone. Only one epiphyseal fragment may be formed. However, the present invention preferably applies to cases where more than one epiphyseal fragments are formed.

Some of the epiphyseal fragments, like fragments 4 and 5 of the present example, may be designated as "tuberosity fragments". These particular fragments are each secured to a muscle of the patient by means of a tendon of the concerned muscle. In other words, the implantation sites of the concerned muscles are located on these tuberosity fragments.

A muscle 7 is coupled to the external surface 23 of the fragment 4. In the present case, the fragment 4 includes the greater tuberosity of the original bone, originally fixed with a partially-illustrated supraspinatus muscle 7 of the patient.

A muscle 13 is coupled to the external surface 24 of the fragment 5. In the present case, the fragment 5 includes the lesser tuberosity of the original bone, originally fixed with a partially-illustrated subscapularis muscle 13 of the patient.

Some other epiphyseal fragments, like fragment 6 of the present example, may be designated as "articular fragment". Each articular fragment is initially part of a joint of the patient, for articulating the long bone with an auxiliary bone of the patient.

Figure 2:
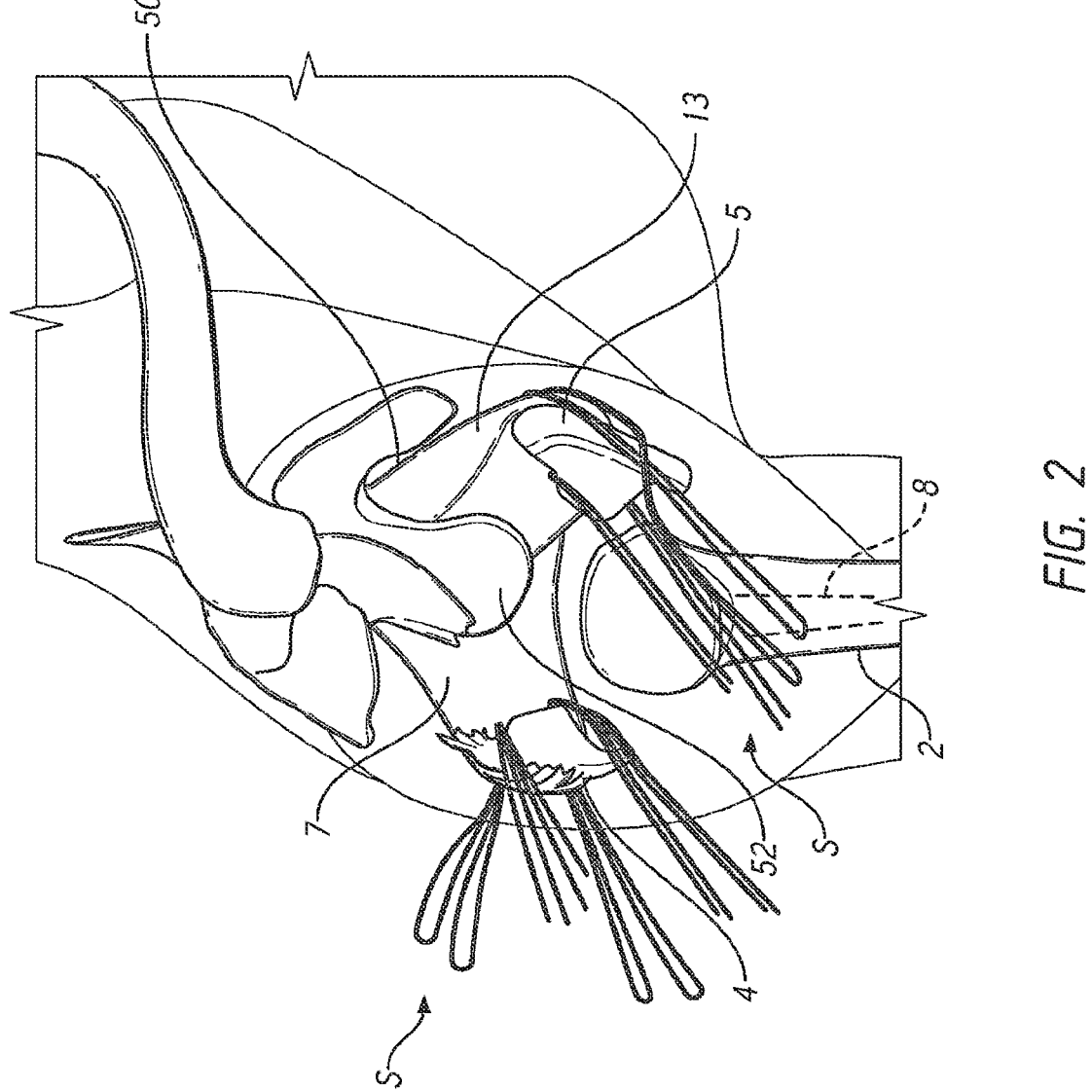
FIG. 2 is a schematic view of a human shoulder joint where the proximal humerus has suffered a fracture, separating into at least four bone segments.

In the present case, the articular fragment 6 is a humeral head of the humerus, which is originally part of the shoulder joint, for articulating the humerus with a scapula 50 of the patient (see FIG. 2). In this case, the scapula forms the "auxiliary bone" of the shoulder joint. More precisely, the external surface 25 of the humeral head 6 has a generally spherical and convex shape and is initially articulated with a corresponding concave surface of a glenoid part 52 of the scapula 50.

Should some fragments have cracks or have geometrical defects may be spatially reconstructed with bone graft, cement or any other suitable replacement material. In the present example, fragment 4 comprises a portion 70 of replacement material for filling a notch of the fragment 4. In this case, the portion 70 forms a part of the edge of the fragment 4, considered as a part of the fracture line 41, for the sake of simplicity.

As visible in FIG. 1, a prosthesis 11 comprises a stem part 12 and advantageously a head part 14. In the case the fractured long bone is a humerus, the prosthesis 11 constitutes a shoulder prosthesis, or at least a humeral component of a shoulder prosthesis. This prosthesis 11, at least the stem part 12, is patient-specific. In other words, the prosthesis 11 is designed depending on the geometry of the fractured long bone of one specific patient, the prosthesis 11 being intended to be implanted into this particular patient.

In one embodiment, the stem part 12 comprises:
a coverable diaphyscal portion 16, forming a distal end of the stem part 12 along axis X12; and
coverable epiphyseal portions 20, 21 and 22, located at a proximal end of the stem part 12 along axis X12.

In some embodiments, the portions 16, 20, 21 and 22 form a single integral piece. In some other embodiments, one or more portions may be a separate piece assembled with the others.

The stem part 12 is configured to be inserted into the medullary cavity 8 of the diaphyseal fragment 2, through the open proximal end 10, as depicted with the arrow A8, along or parallel to axis X2. The stem part 12 preferably defines the axis X12, that is along, parallel to or coaxial with axis X2 when the stem part 12 is secured to the fragment 2. This insertion of the stem part 12 preferably ensures securing the stem part 12 to the fragment 2. In some embodiments, supplementary means may be used for reinforcing the securing, such as cement, fasteners, or other means.

The coverable diaphyseal portion 16 is configured for securing the stem part 12 to the fragment 2, preferably by fitting or anchoring of the portion 16 into the medullary cavity 8. At least, the portion 16 has a shape that corresponds to the shape of the medullary cavity 8, specifically to this patient. The portion 16 is configured so that its exterior surface is covered, e.g., entirely covered, by the diaphyseal fragment 2 when the stem part 12 is secured to the diaphyseal fragment 2, whereas the rest of the stem part 12, located at a proximal end of the stem part 12, is left uncovered by the diaphyseal fragment 2. In this case, "the rest of the stem part 12" includes the coverable epiphyseal portions 20, 22 and 24.

When inserted into the medullary cavity 8, the stem part 12 applies mechanical stress to the fragment 2, to an extent than may be chosen in advance prior or during designing of the prosthesis 11, thanks to a method explained below. In the present example, the stem part 12 is configured so that the predetermined mechanical stress is applied to a contact zone 40 of the fragment 2, also chosen in advance. This zone 40 is formed at the surface thereof, inside the cavity 8, as depicted in FIG. 1. This zone 40 is entirely in contact with the portion 16 of the stem part 12. The zone 40 may be a continuous contact zone.

The zone 40 preferably extends all around axis X2, drawing a ring-like shape. In other words, the zone extends continuously along a circumference of the medullary cavity around axis X2.

In other embodiment, the mechanical stress may be applied to several distinct zones of the cavity 8. The distinct zones may be spaced apart and not continuous with each other. The distinct zones can be disposed about a circumference of the cavity 8 at one location of the axis X2. The distinct zones can be two or more continuous peripheries of the cavity 8 spaced apart from each other along the axis X2. The distinct zones can be non-continuous about the circumference and spaced apart along the axis X2.

In any case, the amount of mechanical stress to be applied is chosen in advance, the contact zone is chosen in advance, and the prosthesis is manufactured so that said chosen mechanical stress is actually applied onto said chosen contact zone 40 when the prosthesis 11 is secured to the fragment 2. Thus, the prosthesis is made patient-specifically with regard to contact in the cavity 8. An appropriate mechanical stress may be applied onto the diaphyseal fragment 2 so as to avoid osteonecrosis, or any other consequence relative to a lack of osseous mechanical loading.

In the present invention, by "mechanical stress" applied to a bone fragment, it is meant a mechanical stress sufficient to avoid osseous necrosis. The mechanical stress applied to the bone fragments is also chosen not to exceed the mechanical resistance of the bone fragments. In other words, the mechanical stress is chosen not to break or fracture the bone fragments. The appropriate stress to be applied may be calculated depending on the geometry of the considered bone fragments and on the osseous density of these fragments. For example, the mechanical stress may be a pressure exerted onto the considered bone fragment, traction, flexion or the like.

Preferably, the mechanical stress is distributed evenly on the contact zone 40, or on the contact zones if several contact zones are foreseen. In other words, a same amount of stress is applied to any part of the contact zone 40 or zones. Preferably, the mechanical stress is applied in radial outward directions around axis X12 by the coverable portion 16 onto the zone 40.

In order to be able to apply the appropriate amount of stress onto the contact zone and to choose what zone of the medullar cavity should serve as the contact zone, a specific method of manufacturing is performed for obtaining the patient-specific prosthesis 11.

Figure 3:
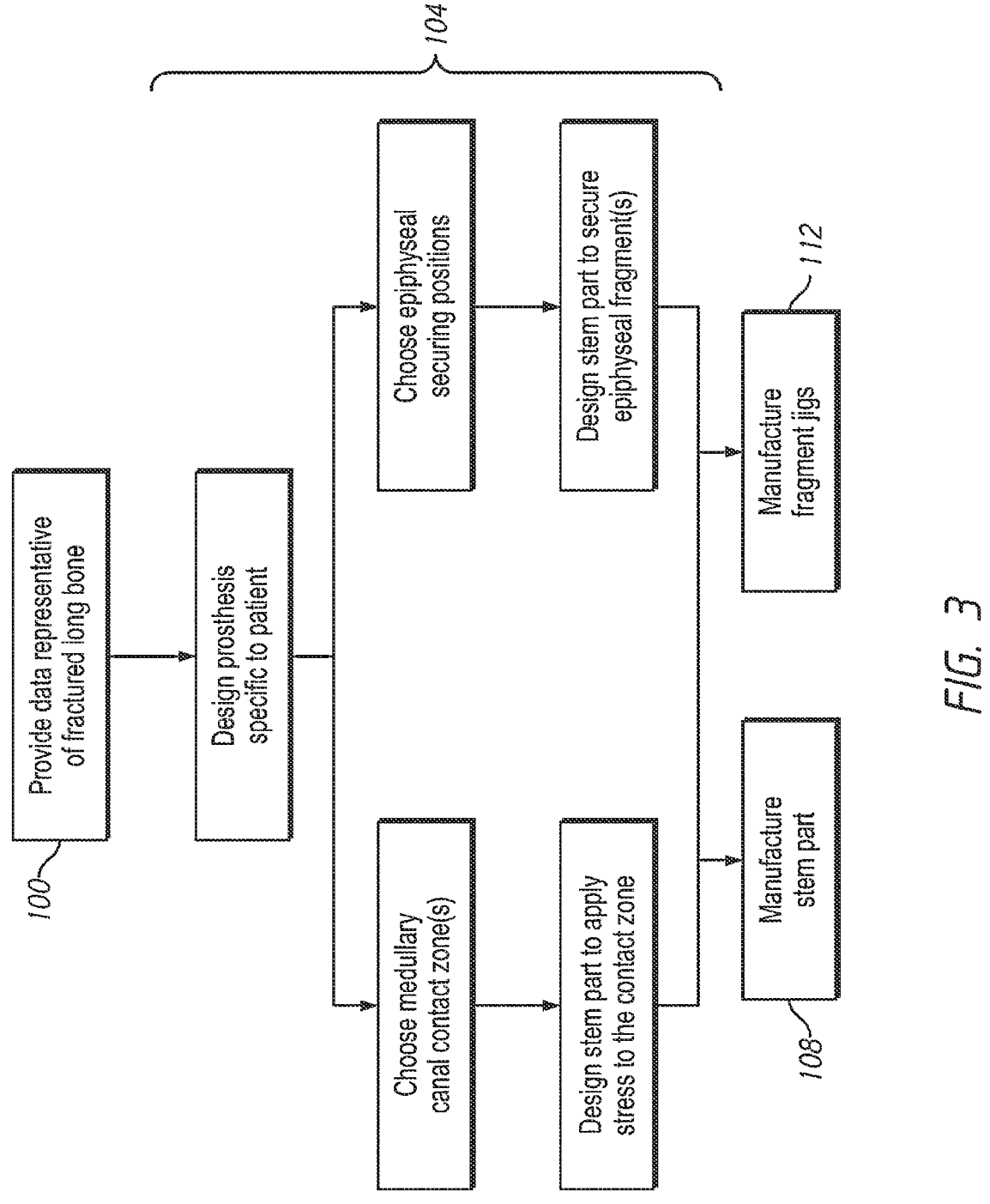
FIG. 3 illustrates a system for making components of patient specific prostheses and related tools.

FIG. 3 illustrates a method according to certain embodiments. For each prosthesis to be obtained and each patient to be treated, the method comprises a preliminary step 100 of providing data representative of the fractured long bone of this patient, including essentially information relative to geometry of the diaphyseal fragment 2. The information may also be relative to the osseous density of the fragment 2.

Preferably, this step of providing data is at least partially achieved by scanning the relevant part of the patient including the fractured long bone, for example with a method of CT-scan ("computerized tomography").

Successively to step 100, based on the data gathered at step 100, a step 104 of the method is performed. The step 104 can involve designing a prosthesis, e.g., the stem part 12, to be specific to the patient. The step 104 includes, in one embodiment, sub-steps of choosing:

which zone or zones of the medullary cavity 8 need to be stressed, and the magnitude of the stress to be applied onto said zone.

Once the zone and the magnitude of the stress are chosen, the stem part 12 of the prosthesis is further designed accordingly, during a subsequent sub-step of step 104. The designed stem part 12 is designed so as to be in contact with the chosen zone, becoming the aforementioned contact zone or zones 40, so as to apply the chosen stress or pressure, when effectively mounted to the epiphyseal fragment.

Thus, the step 104 allows designing the prosthesis 11, including in particular the stem part 12, specifically to the patient intended to receive this prosthesis 11.

During a step 108 of the method, successive to the step B, the prosthesis 11 is manufactured, including the stem part 12 as it was designed during the second step. Thus, the patient-specific prosthesis 11 is obtained, for a specific patient.

The step 108 of manufacturing preferably includes additive manufacturing of the entire stem part 12. In some embodiment, only portions of the stem part 12 that are required to be patient-specific, such as the exterior surface in contact with the contact zone 40, are manufactured by additive manufacturing, these patient specific portions being combined with standard portions for forming the stem part 12.

For the present invention, any part obtained by additive manufacturing may be metallic. In some embodiments, appropriate plastic material may be used.

Preferably, the stem part 12 comprises a visible mark 18 as visible in FIG. 1. The visible mark 18 is formed at the exterior surface of the stem part 12. The mark 18 may be a shallow carving, an embossed marking, a colored marking, or the combination thereof, on the surface of the stem part 12. In any case, the mark 18 is configured to be visible to the eye of the surgeon during surgery. The mark 18 preferably forms a line, continuous or dashed. Instead, the mark 18 may form a dot, or several dots. The mark 18 can be formed as part of the step 108.

The mark 18 visually delimits the coverable diaphyseal portion 16 from the rest of the stem part 12. The prosthesis 11, in particular the coverable portion 16 and the mark 18, is designed specifically to the patient so that, when the stem part 12 is inserted into the cavity 8 properly, in particular at the right position relative to the fragment 2 along the diaphyseal axis X2, the mark 18 and the fracture line 9 are superposed. Thus, during surgery, the surgeon is informed by the mark 18 whether the stem part 12 is properly positioned into the cavity 8, at least concerning the position of the stem part 12 relative to the fragment 2 along the axis X2. Also, the shape of the mark 18 may indicate to the surgeon whether the stem part 12 is properly positioned relative to fragment 2, around axis X2. For example, the mark 18 may indicate with a dot, or have a portion reproducing the shape of, a differential pattern around axis X2, such as a dent or a notch, of the fracture line 9. The surgeon has to ensure that the dot or the portion is aligned with the dent, notch or other visually distinct portion of the fracture line 9 identifying a unique rotational position about the axis X2.

Preferably, a correct position of the stem part 12 is obtained when the mark 18 and the fracture line 9 are aligned and/or superposed along and/or about the axis X2. In case of misalignment, the surgeon may adjust the position of the stem part 12 relative to the fragment 2 during surgery. Thus, the mark 18 promotes adequate positioning of the stem part 12, and makes surgery easier. In this adequate positioning, the chosen stress is sure to be applied to the chosen contact zone 40 by the stem part 12 onto the fragment 2.

For obtaining the mark 18 disclosed above, the data of the patient provided during the preliminary step 100 of the method of FIG. 3 is used. During the step 104 of designing the prosthesis 11, the stem part 12 is designed including the coverable diaphyscal portion 16 and the mark 18, so that they may achieve the above-disclosed functions. In particular, the stem part 12 is designed so that the mark 18 delimits the coverable diaphyseal portion 16 and/or indicates where the fracture line 9 is foreseen to be located when the stem part 12 is inserted into the medullary cavity 8, and the bone of the fragment 2 covers the portion 16. When so received and positioned in the medullary cavity 8, the stem part 12 applies the chosen stress to the zone 40 in the cavity 8.

In an embodiment of the method of FIG. 3, the portion 16 of the stem part 12 is configured to be radially outwardly expansible around axis X12. The expansion may be activated by the surgeon in a method of using the stem part 12. For example, the stem part 12 is designed and manufactured including an expansion screw 60, coaxial with axis X12. The screw may be actuated from outside of the portion 16 by the surgeon: for example the screw head is accessible from the opposite end of the stem part 12. The stem part 12 may be introduced into the cavity 8 to the desired position, and then, the surgeon may actuate the screw 60 for expanding the stem part radially outwardly, so that the stem part applies the chosen mechanical stress onto the zone 40. Any other suitable stem part expansion actuator than the screw 60 may be provided instead. The method of FIG. 3 can include within step 104 designing the actuatable device, e.g., the screw 60 and corresponding threads and structure of the stem part 12 such that a selected number of turns or advancement of the screw provides the designated stress onto the zone or zones 40.

The stem part 12 is configured for receiving the epiphyseal fragments 4, 5 and 6. In other words, these fragments 4, 5 and 6 may be secured to the stem part 12.

Specifically to the patient, the stem part 12 is designed so as to ensure a patient-specific positioning of the fragments 4, 5 and 6 relative to the stem part 12 and to each other. The positioning of the fragment 2 relative to the stem part 12 may also be planned patient-specifically, as explained above, so that eventually, the fragments 2, 4, 5 and 6 are positioned relative to each other in a chosen manner when secured to the stem part 12. As concerns the fragments 4, 5 and 6, the stem part 12 is designed so that the fragments are positioned at chosen securing positions, defined in advance, specifically to the patient. In particular, this positioning is chosen specifically to the shape of the fragments 4, 5 and 6, and preferably also to the shape of the fragment 2.

In the method of manufacturing the prosthesis 11, step 100 may include providing data relative to the fragments 4, 5 and 6 of the long bone of the patient. This may be performed alternatively or additionally to providing data relative to the fragment 2. The data provided may be relative to the shape of the fragments 4, 5 and 6. The data may also be relative to the osseous density of the fragments 4, 5 and 6. The data for fragments 4, 5 and 6 may be obtained by CT scanning, as explained above for fragment 2.

Step 104 may include a sub-step of choosing, specifically to the patient, respective securing positions of the fragments 4, 5 and 6. The chosen securing positions illustrate how the fragments 4, 5 and 6 will be positioned relative to each other when secured to the stem part 12. The chosen securing positions may depend from the actual size and shapes of the fragments 4, 5 and 6 of the considered patient.

This sub-step of choosing the securing positions may be performed alternatively (as shown in FIG. 3) or additionally to the sub-step of choosing the contact zone 40 for fragment 2. If the sub-step of choosing the securing positions is in addition to the sub-step of choosing the contact zone 40, either the contact zone(s) may be chosen first, the securing positions may be chosen first or these aspects of the stem may be configured iteratively or simultaneously.

In one example, once the securing positions are chosen, the sub-step of designing the stem part 12 can be performed, so that the stem part 12 is configured for securing the epiphyseal fragments at the respective chosen securing positions. In other words, the designed stem part enables or even imposes that, when the fragments 4, 5 and 6 are secured thereto, they are in the planned positions.

Then, during step 108, the prosthesis 11, including in particular the stem part 12 with the features designed in step 104 above, is manufactured.

The fragments 4, 5 and 6 are configured to be positioned onto the stem part 12 as illustrated in FIG. 1 with the arrows A4, A5 and A6, respectively.

When the fragments 4, 5 and 6 are secured to the stem part 12, each coverable epiphyseal portion 20, 21 and 22 is configured for being essentially covered, preferably completely covered, by one of the epiphyseal fragments 4, 5 and 6, respectively. Preferably, for receiving the fragments 4, 5 or 6, each respective coverable portion 20, 21 and 22 has an external surface, shaped in correspondence to an internal surface 27, 28 or 29 of the respective concerned fragment 4, 5 or 6. When received properly, namely according to the chosen securing position, each fragment 4, 5 and 6 preferably entirely covers the exterior surface of the concerned portion 20, 21 and 22. For this purpose, the portions 20, 21 and 22 of the stem part 12 are designed patient specifically during step 104.

Preferably, the stem part 12 is designed so that the reattached fragments 4, 5 and 6 are positioned in their original position relative to each other and to the diaphyscal fragment 2, as at the time when the bone was not yet fractured.

In an alternative embodiment, the stem part 12 may be configured so that one or more of the fragment 2, 4, 5 and 6 is planned to be in a different position than its original position relative to the other fragments.

Preferably, the stem part 12 is designed so that the fragments 2, 4, 5 and 6 bear against each other by means of their respective fracture lines 9, 41, 42 or 43 when they are secured to the stem part 12. Thus, the chosen securing positions are preferably positions where the fragments 4, 5 and 6 bear against each other, and optionally at least one of said fragments 4, 5 and 6 bear against fragment 2. At least two of the fragments 2, 4, 5 and 6 bear against each other in this manner. For example, when secured to the stem part 12, fragment 4 is in abutting contact with fragment 5, the fracture line 41 being in abutting contact with the fracture line 42. When secured to the stem part 12, and when fragment 4 is in abutting contact with fragment 5, the fracture line 41 also can be being in abutting contact with the fracture line 9. When secured to the stem part 12, and when fragment 4 is in abutting contact with fragment 5, and the fracture line 41 is in abutting contact with the fracture line 9, the fracture line 42 also can be being in abutting contact with the fracture line 9.

In an embodiment, the stem part 12 is designed with a chosen securing position for the fragments 4, 5 and 6, enabling that the fragments 4, 5 and 6, and optionally fragment 2, apply mechanical stress to each other when the fragments 2, 4, 5 and 6 are actually positioned at these chosen securing positions.

For example, the stem part 12 is designed so that positioning the fragment 4 at its securing position on the stem part 12 will result in the fragment 4 being compressed between fragments 2, 5 and 6, if the fragments 2, 5 and 6 are also positioned at their respective securing positions. In this case, the fragment 2, 5 and 6 apply mechanical stress to the fragment 4 by means of their respective fracture lines 9, 42 and 43, onto the fracture line 41 of the fragment 4. In this case, resulting mechanical stress is also applied onto the fragments 2, 5, and 6. This mechanical stress is achieved by planning an adequate positioning of the fragments 2, 4, 5 and 6 relative to each other. Specifically, the stem part 12 may be designed so that the fragments 2, 4, 5 and 6 must be tightly fitted against each other by the surgeon when secured to the stem part 12 at their respective chosen securing positions. The amount of mechanical stress to be applied to each fragment 2, 4, 5 and 6 by one or more other of these fragments may also be chosen by appropriate designing of the stem part 12 and choice of positioning of the fragments.

Thus, choosing the securing positions during step 104 is made so that the abovementioned mechanical stress, with a chosen magnitude, is applied on the fragments 4, 5 and 6 when actually positioned this way. Thus, the obtained prosthesis 11 avoids osteonecrosis by submitting the reattached fragment to an appropriate mechanical stress.

For ensuring that the planned positioning of the fragments 4, 5 and 6 is achieved, the exterior surface of the stem part 12, in particular for the portions 20, 21 and 22, preferably has a shape corresponding to the shape of fragments 4, 5 and 6, in particular corresponding to the surfaces 27, 28 and 29 of said fragments. The surgeon is informed that one epiphyseal fragment is correctly positioned, according to the chosen securing position, if the epiphyseal fragment fits onto the stem part 12. In case of incorrect positioning of the epiphyseal fragment, said fragment does not fit with the stem part 12.

Additionally or alternatively, for ensuring that the chosen securing position of the fragments 4, 5 and 6 is achieved, in the example illustrated in FIG. 1, the stem part 12 may comprise three plugs 30, 31 and 32, each constituting a distinct securing element of one of the fragments 4, 5 and 6, respectively. Each plug 30, 31 and 32 protrudes from the exterior surface of one of the portions 20, 21 or 22, respectively. Each plug is preferably frustoconical, pyramidal, or shaped as a dome. Conversely, each fragment 4, 5 and 6 may have a blind bore, provided on its internal surface 27, 28 and 29 respectively. These blind bores are preferably drilled or carved in the fragments 4, 5 and 6 by the surgeon with a specific tool. The shape of each bore corresponds to the shape of the plugs 30, 31 and 32, so that each plug may be inserted into the bore of one fragment 4, 5 or 6 when the concerned fragment 4, 5 or 6 is positioned on the stem part 12. Thus, when the plug is inserted into the appropriate bore of a given fragment 4, 5 or 6, the surgeon is sure that this fragment is correctly positioned onto the stem part 12.

Preferably, the methods of manufacturing includes a step 112 of designing and/or manufacturing one or more patient-specific jigs, depending on the chosen securing position and on the data representative of the patient. Each jig, for example embodied as a drill guide, may be used by the surgeon for drilling the blind bore on one of the epiphyseal fragments. Each jig is adapted to the shape of the bone fragments to be reworked by the surgeon. Thus, the surgeon is sure to drill the blind bores at the appropriate position on the fragments 4, 5 and 6, thus enabling a positioning of the fragments 4, 5 and 6 at the chosen securing positions.

In a preferable embodiment, the plugs are configured so as to apply mechanical stress onto the fragments 4, 5 and 6. For example one of the epiphyseal fragments may be compressed between the plug, on which it is mounted, and another epiphyseal fragment. In this example, the plug applies radially directed mechanical stress to the blind bore of the epiphyseal fragment and said fragment receives mechanical stress onto the fracture line in an opposed direction due to reaction force at the fracture line. Thus, the risk of osseous necrosis is reduced by the applications of these stresses.

Furthermore, the plugs may be designed so as to apply mechanical stress to the blind hole of the fragment by tight fitting into the blind hole.

More than one plug may be provided for each epiphyseal portion, and a plurality of plugs may be provided for positioning each epiphyseal fragment.

In some embodiments, the plugs are formed integral with the concerned epiphyseal portion. Alternatively, one or more of the securing element may be a separate part assembled with the concerned epiphyseal portion.

In some embodiments, instead of the aforementioned plugs, any other type of positioning element may be provided.

Additionally or alternatively, the stem part 12 comprises a visible mark 45 indicating the respective chosen securing positions of the epiphyseal fragments 4, 5 and 6 on the stem part. The visible mark 45 is formed at the exterior surface of the stem part 12. The mark 45 may be a shallow carving, an embossed marking, a colored marking, or the combination thereof, on the surface of the stem part 12. In any case, the mark 45 is configured to be visible to the eye of the surgeon during surgery. The mark 45 preferably forms one or more lines, continuous or dashed. Instead, the mark 45 may form one or more dots.

In a preferred embodiment, as illustrated on FIG. 1, the mark 45 visually delimits the coverable epiphyseal portions 20, 21 and 22 from each other and optionally from the rest of the stem part 12. The coverable portions 20, 21 and 22 and the mark 45 are designed specifically to the patient so that, when the fragments 4, 5 and 6 of this patient are positioned at the planned position on the stem part 12, the fracture lines 41, 42 and 43 are superposed with the mark 45. In this aspect, the chosen securing positions are indicated by the mark 45. During surgery, the surgeon is informed by the mark 45 whether the fragments 4, 5 and 6 are properly positioned on the stem part 12.

Thus, the mark 45 promotes adequate positioning of the fragments 4, 5 and 6, and makes surgery easier.

For obtaining the mark 45 disclosed above, the data of the patient provided during the step 100 of the method is used. During the step 104, the stem part 12 is designed including the coverable portions 20, 21, 22 and the mark 45, so that they may achieve the above-disclosed functions. In particular, the stem part 12 is designed so that the mark 45 delimits the coverable epiphyseal portions 20, 21 and 22 from each other and/or indicates where the fracture lines 41, 42 and 43 are foreseen to be located when the fragments 4, 5 and 6 are positioned according to the chosen securing positions.

For securing the fragments 4, 5 and 6 to the stem part 12, further conventional means suitable to the situation may be used, such as fasteners, cement and/or sutures S (see FIG. 2).

The surgeon may decide that the initial articular fragment 6 is reattached to the stem part 12, as disclosed above. In this situation, the head part 14 is optional. For this situation, the prosthesis 11 may be provided without such head part 14.

Or, the head part 14 can be included but the surgeon may determine intraoperatively that the head part 14 is not needed.

In some specific cases, the surgeon may decide that some of the epiphyseal fragments are viable and may be reattached to the stem part 12 and some other fragments are damaged and may not be reattached. In this case, the damaged epiphyseal fragments may require to be replaced with prosthetic means.

In the case the articular fragment 6 is damaged, while the fragments 4 and 5 are viable, the fragment 6 may be replaced by the prosthetic head part 14 shown in FIG. 1. Thus, the head part 14 is configured to be secured to the prosthetic stem part 12 so as to replace the damaged articular fragment 6 when the prosthesis 11 is introduced in the patient's body. The head part 14 is preferably secured at portion 22 of the stem part 12. The securing may be achieved with fasteners or any other suitable securing means. In the case the head part 14 is provided, the plug 32 is optional. Appropriate securing means may be provided on the portion 22 additionally or alternatively to plug 32.

In this case, the method comprises, during step 100, providing data relative to the viable fragments 4 and 5 and to the damaged fragment 6. Then, during step 104, the prosthesis 11 is designed specifically to the patient, including the stem part 12 and the head part 14 being patient-specific.

In the case a head part 14 is used instead of reattaching the fragment 6, the method is similar than the previously explained method. Step 104 includes a sub-step of choosing, specifically to the patient, respective securing positions of the viable fragments 4 and 5 and of the head part 14 relative to each other, and advantageously, relative to fragment 2. In other words, in this sub-step, the position of the head part 14 is chosen, instead of the position of the reattached fragment 6 for the case explained above. The chosen "securing positions" are representative of how the viable fragments 4 and 5 and the head part 14 are planned to be effectively positioned relative to each other when secured to the stem part 12 by the surgeon. The fragments 4 and 5 and the head part 14 are configured to be positioned onto the stem part 12 as illustrated in FIG. 1 with the arrows A4, A5 and A14, respectively. The fragments 4 and 5 are positioned as disclosed above. The fragment 6 can be replaced by the head part 14. Thus, the head part 14 can be positioned in a similar way than the fragment 6 of the previous case. When secured to the stem part 12, the head part 14 preferably substantially or completely covers the portion 22.

In this case, once the securing positions are chosen, the sub-step of designing the stem part 12 is performed. The head part 14 may also be designed patient-specifically. In this designing sub-step, the stem part 12, and optionally at least a part of the head part 14, is designed so that the stem part 12 allows securing the fragments 4 and 5 and the head part 14 at the chosen securing positions. In other words, the designed stem part 12 enables or even imposes that, when the fragments 4 and 5 the head part 14 are secured thereto, they are in the planned positions.

Then, during step 108, the prosthesis 11, including in particular the stem part 12 with the features designed in step 104 above, is manufactured. If all or part of the head part 14 is designed patient-specifically during step 104, the patient specific features of the head part 14, or all the head part 14 is also manufactured during step 108.

The head part 14 may comprise a standard cap 50. "Standard" means that the cap 50 is not patient-specific, although a cap of appropriate size and shape may be chosen among a definite collection of standard caps. Thus, the standard cap 50 is provided or manufactured separately from the patient-specific features manufactured at step 108.

The standard cap 50 comprises an articular surface 52 of convex shape, preferably spherical, for forming a prosthetic joint of the patient, combined with the glenoid cavity of the scapula of the patient, or any other auxiliary bone considered, in replacement for the surface 25 of fragment 6. In other words, the cap 50 may be shaped as a dome as depicted in FIG. 1. By "prosthetic joint", it is meant that at least a part of the joint is prosthetic. In this case, the standard cap 50 is a prosthetic part of the joint.

Alternatively to a convex shape, depending on the situation, a concave shape may be used.

The standard cap 50 also comprises a trunnion 55, shown in dashed lines in FIG. 1, protruding in an opposed to the surface 52.

The standard cap 50 also comprises a securing surface 54, opposed to the surface 52 and formed at the end of the trunnion 55. The standard cap 50 is configured to be secured to the stem part 12 by means of the securing surface 54.

The head part 14 also comprises a patient-specific insert 56. This insert 56 is patient specifically designed during step 104 according to the data provided at step 100, and manufactured during step 108 according to this design. The insert 56 is a separate piece from the cap 50 and is assembled with it before or during surgery.

The insert 56 is interposed between the cap 50 and the stem part 12. More precisely, the insert 56 has a surface 57 bearing against a border surface 53 of the cap 50. The border surface 53 surrounds the trunnion 55, and is opposed to the surface 52. The insert 56 also has an opposed surface 58, that is configured to bear against the fracture lines 41 and 42 of the fragments 4 and 5. The insert 56 is preferably shaped as a ring or a washer, as depicted in FIG. 1, so that the cap 50 may be secured to the stem part 12 through the insert 56. In this case, the trunnion 55 passes through a central hole of the insert 56. The insert 56 is preferably fitted, for example conically fitted, onto the trunnion 55.

Alternatively, the cap of the head part 14 is made patient-specifically, designed during step 104 and manufactured during step 108. In this case, the cap and the insert may form a single piece instead of two distinct assembled pieces.

During step 104, the respective securing positions of fragments 4 and 5 and of the head part 14 are chosen so that a respective chosen mechanical stress is applied to each fragment 4 and 5 by the head part 14. In a preferable embodiment, the fragments 4 and 5 are compressed between the head part 14 and the fragment 2. Alternatively, the head part 14 may apply mechanical stress on the fragments 4 and 5 without relying on the fragment 2.

More specifically, step 108 may include patient-specifically designing the insert 56 so that the insert 56 applies the respective stress onto the fragments 4 and 5 with a chosen magnitude. In particular, the shape of the surface 58 may be designed in correspondence with the shape of the fracture lines 41 and 42, so that the surface 58 may distribute the applied stress along the fracture lines 41 and 42.

Thus, when the prosthesis 11 is manufactured and implanted in the patient, a mechanical stress defined in advance patient specifically is applied to the reattached fragments 4 and 5, and optionally to the fragment 2, by the head part 14, and optionally by the stem part 12.

The patient specific parts of the head part 14 may be obtained, during step 108, by additive manufacturing. Preferably, the insert 56 is manufactured by additive manufacturing. If the cap 50 is patient-specific, the insert 56 and the cap 50 may both be obtained by additive manufacturing.

Instead of having a patient specific surface 58, the head part 14 may be chosen standard. Thus, only the relative securing position of the fragments 4 and 5 and of the head part 14 may allow defining the mechanical stress to be applied.

FIG. 3 shows a system schematically illustrates a planning system 120 that can be used in the method of FIG. 2 and other corresponding methods for forming the stem part 12 and/or fragment jigs as discussed in step 112. The stem part 12 and fragment jigs (if provided) are formed as patient specific parts and jigs by referencing pre-operative imaging such as MRI, CT imaging or the like. The planning system 120 receives inputs 122 and produces outputs 124 including the stem part 12. The inputs 122 include pre-operative shoulder images 126 and patient input information 128. The pre-operative shoulder images 126 can include MRI, CT imaging and other information that allows the planning system 120 to render or characterize at least the fragments 2, 4, 5, and 6. For example, the pre-operative shoulder images 126 can include the location, shape, and orientation of any of the fracture lines 9, 41, 42, 43, as well as other features such as rotational orientation landmarks of the proximal end 10 of the fragment 2. The pre-operative shoulder images 126 can include information about the location, shape and orientation of landmarks of any of the fragments 2, 4, 5, and/or 6 or other parts of the bones of the joint being treated. In the case of the shoulder, the images 126 can include location, orientation or other characterizing information about portions of the humerus such as the surface contour of the canal 8, the greater tubercle, the lesser tubercle, the surgical neck, the bicipital groove or other landmarks of the proximal humerus.

The patient input information 128 can include the patients name, the shoulder being treated, other past and future therapies and other information relevant to the procedure.

The planning system 120 can include a number of modules that can process the inputs 122. The planning system 120 can include a module 130 for selecting among reverse and anatomic implant configuration. The planning system 120 can include a module 132 configured to define stem shape as rotationally symmetric or asymmetric. A stem shape module 132 can also define the taper line of the stem part 2 along the longitudinal axis thereof The planning system 120 can have a force level module 134 that can determine how much force is appropriate to achieve a lessening of osseous necrosis while not resulting in fracture of fragment coupled with the stem part 12. The system 120 also can include an orientation module 136 that defines the rotational position of the stem part 12 in the canal 8, e.g., by defining a visual relationship between the stem part and a landmark of the fragment 2. Each of these and other features can be determined and prescribed by the planning system 120 and can be incorporated into the outputs 124 of the planning system 120.

The outputs 124 can include the stem part 12, a fragment jig (not shown), an implant identification 140, and patient procedural information 142. The stem part 12 that can be output by the planning system 120 can be a plan for forming the stem part 12 or can be an actual stem part if the planning system 120 is configured with or coupled with a manufacturing facility or manufacturing process 144. In some applications, the process 144 that is used to form the stem part 12 includes additive manufacturing such as three dimensional printing. Examples of three dimensional printing include direct metal laser sintering (DMLS), fused deposition modeling (FDM), fused filament fabrication (FFF), and electron beam melting (EBM). Any one or a combination of these or other additive manufacturing processes can be used in the manufacturing process 144. In these processes a three dimensional object is formed by sequentially forming individual layers of the object on top of previously formed individual layers. These processes can closely control the gross dimensions of the object and also can form complex features and shapes such as contours. As discussed further below, these processes can be used to form complementary surface that can mate with specific anatomy of a specific patient, e.g., concave surfaces that can nest on top of corresponding convex surfaces.

With reference to FIG. 3, the planning system 120 can thus include a processor for receiving the inputs 122. The inputs 122 include the patient input information 128 and the pre-operative shoulder images 126. The processor and software process this information with other selections regarding the implant and the patient's anatomy that can be made by a user regarding the nature of the shoulder procedure. The software can produce data that can be input to the manufacturing process 144 to control the operation thereof. The data can be configured for directing a three dimensional printer or other additive manufacturing process to form the stem part 12. In other approaches the manufacturing process 144 can include multiple steps such as a first step of forming a mold with an additive manufacturing process and thereafter forming the stem part 12 in the mold. These approaches enable the pre-operative images 126 to be utilized to configure patient specific surfaces of the stem part 12 to be complementary/negative surfaces such that the guide is seated according to the optimized fit as determined by the surgeon or other user.

The planning system 120 can also provide implant identification 140 that corresponds to the stem part 12. For example, the planning system 120 can provide a type of implant that the stem part 12 is suitable to mate with. For example, the implant identification 142 identifies an anatomic articular head, such as the head part 14 with a convex articular surface to be coupled with the stem part 12. The implant identification 140 can identify a reverse implant (not shown) to be coupled with the stem part 12 following repair of the fracture. The outputs 124 can include the patient output information 142 which can include not only the name of the patient but also the shoulder to be treated and other specific information about the stem part 12 and/or fragment jigs (not shown) if provided such as which rotational landmarks may be used to position the stem part 12.

After the prosthesis 11 is manufactured at step 108 for the specific patient to be treated, the surgeon may proceed as follows for installing the prosthesis 11 in the patient's body as discussed further below.

Figure 4:
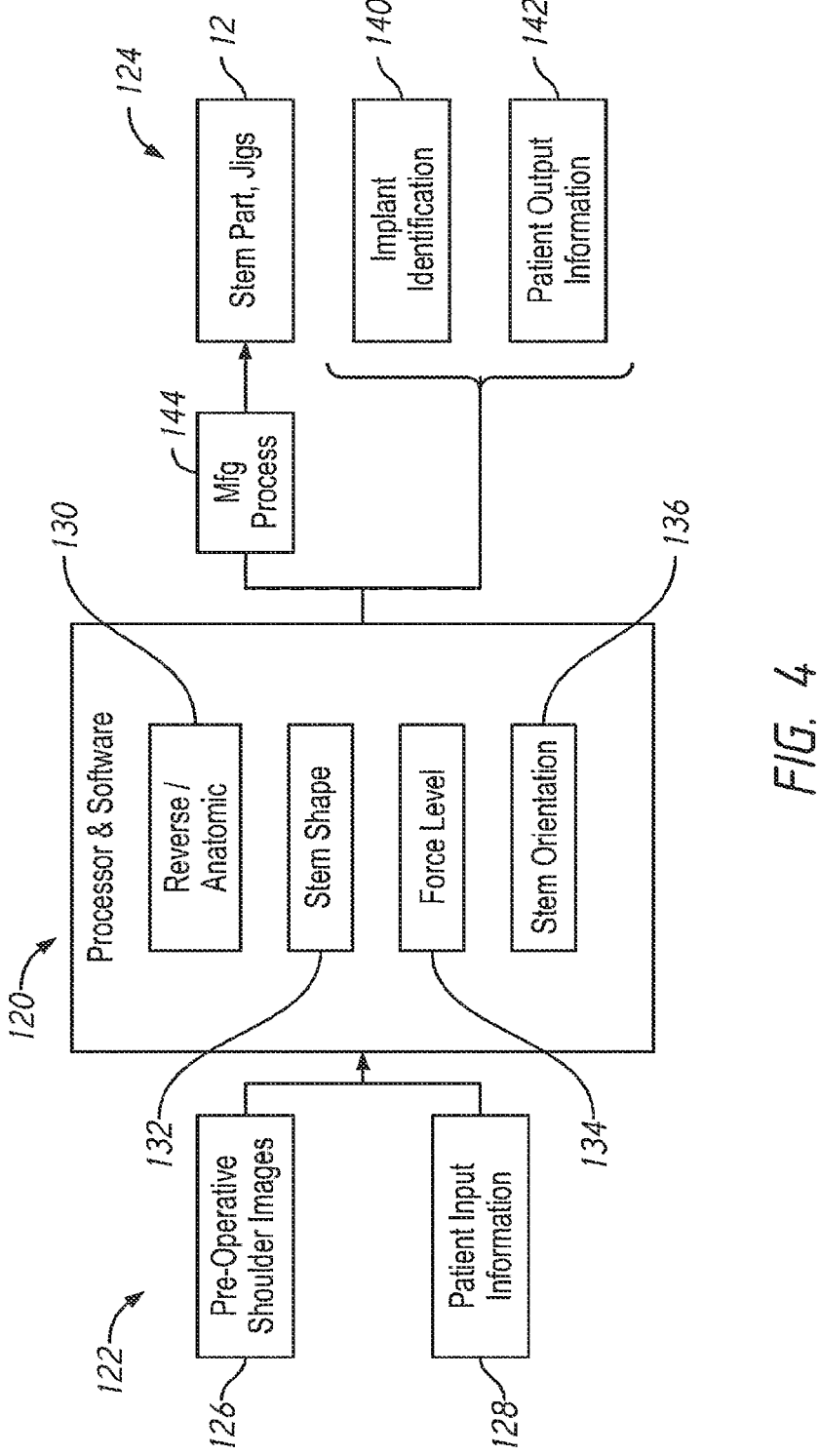
FIG. 4 is a flow chart illustrating a method of making a stem implant and optionally a fragment jig as disclosed herein.
Figure 5:
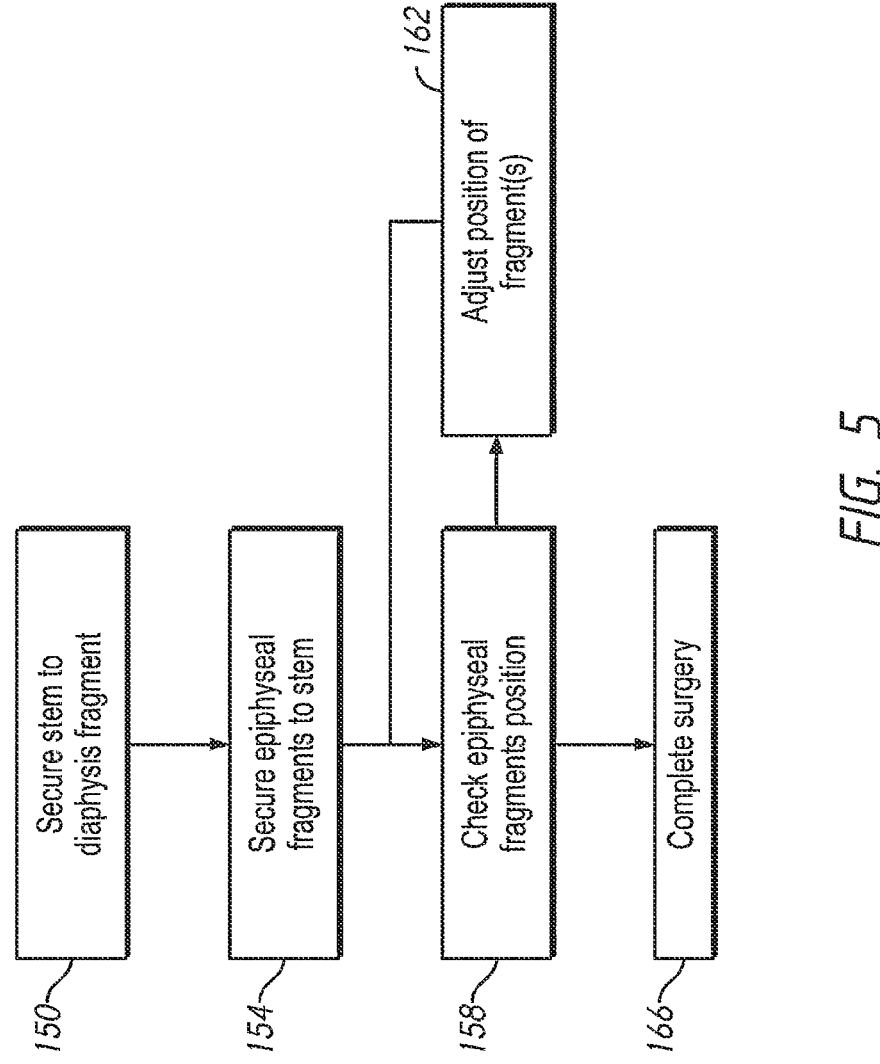
FIG. 5 is a flow chart illustrating a method performing surgery with a stem made according to the methods disclosed herein.

FIG. 4 shows a method of implanting the stem part 12. In a step 150 the surgeon firstly secures the stem part 12 onto the fragment 2, by introduction of the coverable portion 16 into the cavity 8. The surgeon optionally checks that the mark 18 is superposed with the fracture line 9 and may adjust the position of the stem part if necessary. In the adequate position, the stem part 12 applies the chosen mechanical stress to the zone 40 of the cavity 8.

Secondly, in a step 154 the surgeon secures the fragments 4 and 5 onto the stem part 12. For this purpose, the surgeon may have prepared the fragments 4 and 5 in advance, including drilling the blind holes. The blind holes may be drilled with help of a tool and/or a jig made patient-specifically during step 112, designed at step 108 based on the data of step 100. In this case, the fragments 4 and 5 are positioned onto the stem part 12 with the plugs 30 and 31 inserted into the blind holes. In a step 158, the surgeon checks whether the positioning of the fragments 4 and 5 is correct by checking if the fragments 4 and 5 match with the mark 45. If necessary, in a step 162 the position of the fragments 4 and 5 is adjusted by the surgeon with help of the mark 45.

Thirdly, the fragment 6 is secured to the stem part 12. This can involve repeating any of steps 150, 154, 158, and 162. For this purpose, the surgeon may have prepared the fragment 6 in advance, including drilling the blind hole. The blind hole may be drilled with help of a tool and/or a jig made patient-specifically during step 112, designed at step 104 based on the data of step 100. The surgeon checks whether the positioning of the fragment 6 is correct by checking if the fragment 6 matches with the mark 45. If necessary, the position of the fragment 6 is adjusted by the surgeon with help of the mark 45. Securing the fragment 6 applies mechanical stress onto the fragments 4 and 5. The method of FIG. 4 can be completed at step 166 when the fragments, 4, 5, and 6 are all properly placed.

It can be provided that the fragments 4 and 5 are interposed between the fracture line 9 of fragment 2 and the fragment 6. In this case, mechanical stress is also applied to fragment 2 by fragments 4 and 5. In another embodiments, the fragments 4 and 5 are supported by the plugs 30 and 31, onto which the mechanical stress is transmitted, without transmitting the mechanical stress to the fragment 2.

Fasteners, sutures S (as seen in FIG. 2), adhesive means or any suitable means may be used by the surgeon for maintaining the fragments 2, 4, 5 and 6 onto the stem part 12.

If the fragment 6 is to be replaced, said fragment 6 is not secured to the stem part 12. Instead, the head part 14 is secured to the stem part 12. Securing the head part 14 applies mechanical stress onto the fragments 4 and 5, and optionally to the fragment 2, in a similar manner.

Fasteners, sutures S (as seen in FIG. 2), adhesive means or any suitable means may be used by the surgeon for maintaining the fragments 2, 4 and 5 and the head part onto the stem part 12.

The external surface of at least one of the coverable portions 16, 20, 21 and 22 is preferably rough, or even comprises barbs, for helping securing the bone fragments 2, 4, 5 and 6 secured thereto.

Example Embodiments

The following example embodiments identify some possible permutations of combinations of features disclosed herein, although other permutations of combinations of features are also possible.

Embodiment 1.—A method for manufacturing a prosthesis (11) for a fractured long bone of a patient, the method comprising the steps of:
A) providing data representative of the fractured long bone of the patient, the fractured long bone comprising a diaphyseal fragment (2) comprising a medullary cavity (8)
B) based on the data provided at step A), designing the prosthesis (11) specifically to the patient, the prosthesis (11) comprising a stem part (12) configured to be inserted into the medullary cavity (8) for securing the stem part (12) to the diaphyseal fragment (2), step B) comprising:
   a sub-step of choosing, specifically to the patient, at least one contact zone (40) of the medullary cavity (8) onto which a respective chosen mechanical stress is planned to be applied by the stem part (12), when the stem part (12) is inserted into the medullary cavity (8) and
   a sub-step of designing the stem part (12) so that the stem part (12) may be inserted into the medullary cavity (8) and thus apply the chosen mechanical stress to said at least one contact zone (40); and
C) manufacturing the prosthesis (11) including the stem part (12) designed at step B).

Embodiment 2.—The method according to Embodiment 1, wherein said at least one contact zone (40) of the medullary cavity (8) continuously covers a circumference of the medullary cavity (8).

Embodiment 3.—The method according to any one of Embodiment 1-Embodiment 2, wherein during sub-step B1), the chosen mechanical stress is chosen to be evenly distributed onto each of said at least one contact zone (40) of the medullary cavity (8).

Embodiment 4.—The method according to any one of Embodiment 1-Embodiment 3, wherein step B) comprises the further sub-step of, based on the data provided at step A), designing the stem part (12) so that the stem part (12) comprises, specifically to the patient:
   a coverable diaphyseal portion (16), configured to be covered by the diaphyseal fragment (2) when the stem part (12) is secured to the diaphyseal fragment (2), whereas the rest of the stem part (12) is left uncovered by the diaphyseal fragment (2); and
   a first visible mark (18), visually delimiting the coverable diaphyseal portion (16) from the rest of the stem part (12).

Embodiment 5.—The method according to any one of Embodiment 1-Embodiment 4, wherein:
   step A) comprises providing data representative of epiphyseal fragments (4, 5, 6) of the fractured long bone; and
   step B) comprises, based on the data provided at step A), designing the prosthesis (11) so that the stem part (12) is configured for securing at least one of the epiphyseal fragments (4, 5, 6) to the stem part (12).

Embodiment 6.—The method according to Embodiment 5, wherein step B) comprises:
   a sub-step of choosing, specifically to the patient, respective securing positions of the epiphyseal fragments (4, 5, 6) relative to each other, representative of how the epiphyseal fragments (4, 5, 6) are planned to be positioned relative to each other when secured to the stem part (12), the securing positions being chosen so that a respective chosen mechanical stress is applied onto each epiphyseal fragment (4, 5) by at least one of the other epiphyseal fragments (6), when the epiphyseal fragments (4, 5, 6) are secured at the respective chosen securing positions of the stem part (12), and
   a sub-step of designing the stem part (12) so that the stem part (12) is configured for securing the epiphyseal fragments (4, 5, 6) at the respective chosen securing positions.

Embodiment 7.—The method according to Embodiment 6, wherein step B) comprises the further sub-step of designing the stem part (12) so that the stem part (12) comprises a second visible mark (45) indicating the respective securing positions of the epiphyseal fragments (4, 5, 6) on the stem part (12).

Embodiment 8.—The method according to Embodiment 7, wherein step B) comprises the further sub-step of designing the stem part (12) based on the data provided at step A), so that the stem part (12) comprises, specifically to the patient, coverable epiphyseal portions (20, 21, 22), being configured for being covered respectively by the epiphyseal fragments (4, 5, 6) when the epiphyseal fragments (4, 5, 6) are secured to the stem part (12) at the respective securing positions; wherein the second visible mark (45) is designed so as to visually delimit the coverable epiphyseal portions (20, 21, 22) from each other.

Embodiment 9.—The method according to any one of Embodiments 6 to 8, wherein the stem part (12) comprises, for at least one of the epiphyseal fragments (4, 5, 6), a respective plug (30, 31, 32), for securing the concerned epiphyseal fragment (4, 5, 6) to the stem part (12), said at least one plug (30, 31, 32) applying mechanical stress onto the epiphyseal fragment (4, 5, 6) secured thereto.

Embodiment 10.—The method according to any one of Embodiments 1 to 5, wherein:

the epiphyseal fragments (4, 5, 6) comprise:

at least one viable tuberosity fragment (4, 5), secured to a muscle (7, 13) of the patient, the muscle (7, 13) being attached to said at least one viable tuberosity fragment (4, 5) by means of a tendon of the muscle (7, 13) and a damaged articular fragment (6), initially being part of an damaged joint of the patient, for articulating the long bone with an auxiliary bone of the patient;

step B) comprises:

based on the data provided at step A), designing the prosthesis (11) so that:

the stem part (12) is configured for securing said at least one viable tuberosity fragment (4, 5) to the stem part (12), and the prosthesis (11) further comprises a head part (14), being configured to be secured to the stem part (12) in replacement for the damaged articular fragment (6) of the fractured long bone of the patient, a sub-step of choosing, specifically to the patient, respective securing positions of said at least one viable tuberosity fragment (4, 5) and of the head part (14) relative to each other, representative of how said at least one viable tuberosity fragment (4, 5) and head part (14) are planned to be positioned relative to each other when secured to the stem part (12), the securing positions being chosen so that a respective chosen mechanical stress is applied to each of said at least one viable tuberosity fragment (4, 5) by the head part (14), when said at least one viable tuberosity fragment (4, 5) and the head part (14) are secured at the respective chosen securing positions of the stem part (12), and a sub-step of designing the stem part (12) so that said at least one viable tuberosity fragment (4, 5) and the head part (14) may be secured to the stem part (12) at the respective chosen securing positions;

step C) comprises providing or manufacturing the head part (14) of the prosthesis (11).

Embodiment 11.—The method according to Embodiment 10, wherein the head part (14) comprises:

a standard cap (50), comprising an articular surface (52) of concave or convex shape for forming a prosthetic joint for replacement of the damaged joint of the patient, and comprising a securing surface (54) opposed to the articular surface (52), the standard cap (50) being secured to the stem part (12) by means of the securing surface (54);

a patient-specific insert (56), designed during step B) patient specifically, and manufactured during step C), configured to:

be interposed between the standard cap (50) and the stem part (12), and apply the respective mechanical stress onto each of said at least one viable tuberosity fragment (4, 5).

Embodiment 12.—The method according to any one of Embodiment 1-Embodiment 11, wherein step A) includes using CT scans of the patient and step C) includes additive manufacturing of at least a part of the prosthesis (11).

Embodiment 13.—The method according to any one of the preceding Embodiment 1-Embodiment 12, wherein the fractured long bone is a fractured humerus, the prosthesis (11) being a shoulder prosthesis (11).

Embodiment 14.—A patient-specific prosthesis (11) for a fractured long bone of a particular patient, the prosthesis (11) comprising a stem part (12) that is designed based on data representative of the fractured long bone of this particular patient, so as to:

be inserted into the medullary cavity (8) of a diaphyseal fragment (2) of the fractured long bone of the patient for securing the stem part (12) to the diaphyseal fragment (2), and apply a chosen mechanical stress to at least one contact zone (40) of the medullary cavity (8), chosen based on said data.

Embodiment 15.—The patient-specific prosthesis (11) according to Embodiment 14, wherein the stem part (12) comprises, specifically to the patient:

a coverable diaphyseal portion (16), including at least a part of the stem part (12) and being configured to be covered by the diaphyseal fragment (2) when the stem part (12) is inserted into the medullary cavity (8), whereas the rest of the stem part (12) is left uncovered by the diaphyseal fragment (2); and a first visible mark (18), visually delimiting the coverable diaphyseal portion (16) from the rest of the stem part (12).

Terminology

Certain methods are described as sliding a first component relative to a second component. However, it should be understood that relative motion between first and second components can also include sliding the second component relative to the first component. For example, "sliding the intermediate portion in a transverse direction relative to a longitudinal axis of the metaphyseal portion" can also include "sliding the metaphyseal portion in a transverse direction relative to a longitudinal axis of the intermediate portion."

"Implant" is a broad term and is to be given its ordinary and customary meaning to a person of ordinary skill in the art and includes, without limitation, temporary implants (e.g., for trialing) or permanent implants (also referred to herein as definitive implants) for any anatomy, including, but not limited to, shoulder replacements, knew replacements, femoral replacements, and hip replacements.

As used herein, the term "metaphyseal portion" refers to either a reverse metaphyseal portion or an anatomic metaphyseal portion unless otherwise specified.

As used herein, the relative terms "proximal" and "distal" shall be defined from the perspective of the humeral component. Thus, proximal refers to the direction of the metaphyseal portion and distal refers to the direction of the stem portion.

For expository purposes, the term "transverse" as used herein is defined as a direction generally perpendicular to the longitudinal axis of the assembly, unless otherwise specified.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," "generally," and "substantially" as used herein represent an amount close to the stated amount that still performs a desired function or achieves a desired result. For example, the terms "approximately," "about," "generally," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about four" includes "four"

Any methods disclosed herein need not be performed in the order recited. The methods disclosed herein include certain actions taken by a practitioner; however, they can also include any third-party instruction of those actions, either expressly or by implication. For example, actions such as "distally moving a locking element" include "instructing distal movement of the locking element."

Although certain embodiments and examples have been described herein, it will be understood by those skilled in the art that many aspects of the humeral assemblies shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method for manufacturing a prosthesis for a fractured long bone of a patient, the method comprising the steps of:
    providing data representative of the fractured long bone of the patient, the fractured long bone comprising a diaphyseal fragment comprising a medullary cavity;
    based on the data provided, designing the prosthesis specifically to the patient, wherein the prosthesis comprising a stem part configured to be inserted into the medullary cavity for securing the stem part to the diaphyseal fragment, wherein designing the prosthesis further comprises:
    selecting, specifically to the patient, at least one contact zone of the medullary cavity onto which a respective chosen mechanical stress is planned to be applied by the stem part, when the stem part is inserted into the medullary cavity and designing the stem part so that the stem part may be inserted into the medullary cavity and thus apply the chosen mechanical stress to said at least one contact zone; and
    manufacturing the prosthesis including the stem part as designed.

2. The method according to claim 1, wherein said at least one contact zone of the medullary cavity continuously covers a circumference of the medullary cavity.

3. The method according to claim 1, wherein the chosen mechanical stress is evenly distributed onto each of said at least one contact zone of the medullary cavity.

4. The method according to claim 1, wherein based on the data provided, designing the stem part that comprises, specifically to the patient:
    a coverable diaphyseal portion, configured to be covered by the diaphyseal fragment when the stem part is secured to the diaphyseal fragment, whereas remainder of the stem part is left uncovered by the diaphyseal fragment; and
    a first visible mark, visually delimiting the coverable diaphyseal portion from the remainder of the stem part.

5. The method according to claim 1, wherein:
    providing the data representative of the fractured long bone includes providing data representative of epiphyseal fragments of the fractured long bone; and
    based on the data so provided, designing the prosthesis so that the stem part is configured for securing at least one of the epiphyseal fragments to the stem part.

6. The method according to claim 5, further comprising:
    selecting, specifically to the patient, respective securing positions of the epiphyseal fragments relative to each other, representative of how the epiphyseal fragments are planned to be positioned relative to each other when secured to the stem part, the securing positions being chosen so that a respective chosen mechanical stress is applied onto each epiphyseal fragment by at least one of the other epiphyseal fragments, when the epiphyseal fragments are secured at the respective chosen securing positions of the stem part, and designing the stem part so that the stem part is configured for securing the epiphyseal fragments at the respective chosen securing positions.

7. The method according to claim 6, further comprising designing the stem part so that the stem part comprises a second visible mark indicating the respective securing positions of the epiphyseal fragments on the stem part.

8. The method according to claim 7, further comprising designing the stem part based on the data provided, so that the stem part comprises, specifically to the patient, coverable epiphyseal portions, being configured for being covered respectively by the epiphyseal fragments when the epiphyseal fragments are secured to the stem part at the respective securing positions; wherein the second visible mark is designed so as to visually delimit the coverable epiphyseal portions from each other.

9. The method according to claim 1, wherein:

the epiphyseal fragments comprise:

at least one viable tuberosity fragment, secured to a muscle of the patient, the muscle being attached to said at least one viable tuberosity fragment by means of a tendon of the muscle and a damaged articular fragment, initially being part of a damaged joint of the patient, for articulating the long bone with an auxiliary bone of the patient;

wherein the stem part is designed to be configured for securing said at least one viable tuberosity fragment to the stem part, and the prosthesis further comprises a head part, being configured to be secured to the stem part in replacement for the damaged articular fragment of the fractured long bone of the patient, wherein selecting, specifically to the patient, respective securing positions of said at least one viable tuberosity fragment and of the head part relative to each other, representative of how said at least one viable tuberosity fragment and head part are planned to be positioned relative to each other when secured to the stem part, the securing positions being selected so that a respective chosen mechanical stress is applied to each of said at least one viable tuberosity fragment by the head part, when said at least one viable tuberosity fragment and the head part are secured at the respective selected securing positions of the stem part, and designing the stem part so that said at least one viable tuberosity fragment and the head part may be secured to the stem part at the respective selected securing positions; and the method further comprises providing or manufacturing the head part of the prosthesis.

10. The method according to claim 9, wherein the head part comprises:

a standard cap that includes:

an articular surface of concave or convex shape for forming a prosthetic joint for replacement of the damaged joint of the patient; and a securing surface opposed to the articular surface, wherein the standard cap being secured to the stem part by means of the securing surface; and a patient-specific insert, configured to be interposed between the standard cap and the stem part, and apply the respective mechanical stress onto each of said at least one viable tuberosity fragment.

11. The method according to claim 1, wherein providing the data representative of the fractured long bone of the patient includes using CT scans of the patient; and manufacturing the prosthesis includes additive manufacturing of at least a part of the prosthesis.

12. The method according to claim 1, wherein the fractured long bone is a fractured humerus, the prosthesis being a shoulder prosthesis.

13. A method of surgery on a specific patient's joint that has a fractured long bone, the method comprising:

accessing the joint of the specific patient, the fractured long bone having a first articular surface and an auxiliary articular surface on a bone opposite the first articular surface;

providing a stem part of a prosthesis, the stem part being configured for the specific patient to have a diaphyseal surface configured to apply a chosen stress to bone matter in a medullary canal of the fractured long bone; and advancing the diaphyseal portion into the medullary canal of the fractured long bone to apply the chosen stress to the bone matter in the medullary canal of the fractured long bone.

* * * * *